(12) United States Patent
Macken et al.

(10) Patent No.: US 12,383,740 B2
(45) Date of Patent: Aug. 12, 2025

(54) SYSTEM AND METHOD FOR AUTONOMOUSLY ENABLING AN AUDITORY PROSTHESIS

(71) Applicant: Cochlear Limited, Macquarie University (AU)

(72) Inventors: Luk Macken, Mechelen (BE); Jan Raymond Janssen, St Ives (AU)

(73) Assignee: Cochlear Limited, Macquarie University (AU)

( * ) Notice: Subject to any disclaimer, the term of this patent is extended or adjusted under 35 U.S.C. 154(b) by 607 days.

(21) Appl. No.: 17/258,142

(22) PCT Filed: Aug. 23, 2019

(86) PCT No.: PCT/IB2019/057125
§ 371 (c)(1),
(2) Date: Jan. 5, 2021

(87) PCT Pub. No.: WO2020/044191
PCT Pub. Date: Mar. 5, 2020

(65) Prior Publication Data
US 2021/0228879 A1    Jul. 29, 2021

Related U.S. Application Data

(60) Provisional application No. 62/723,210, filed on Aug. 27, 2018.

(51) Int. Cl.
*A61N 1/36*      (2006.01)
*A61N 1/05*      (2006.01)

(52) U.S. Cl.
CPC ....... *A61N 1/36039* (2017.08); *A61N 1/0541* (2013.01)

(58) Field of Classification Search
CPC .................... A61N 1/36039; A61N 1/0541
See application file for complete search history.

(56) References Cited

U.S. PATENT DOCUMENTS

| | | |
|---|---|---|
| 7,502,653 B2 | 3/2009 | Daly |
| 8,625,828 B2 | 1/2014 | Flynn et al. |
| 8,965,017 B2 | 2/2015 | Bryant et al. |
| 8,965,520 B2 | 2/2015 | Botros et al. |
| 2003/0112987 A1 | 6/2003 | Nordqvist et al. |

(Continued)

FOREIGN PATENT DOCUMENTS

| | | |
|---|---|---|
| CN | 101352596 A | 1/2009 |
| CN | 102986251 A | 3/2013 |

(Continued)

OTHER PUBLICATIONS

International Search Report and Written Opinion for PCT/IB2019/057125, mailed Jan. 3, 2020.

(Continued)

*Primary Examiner* — Joseph M Dietrich
(74) *Attorney, Agent, or Firm* — Knobbe Martens Olson & Bear LLP

(57) ABSTRACT

A method is provided which includes determining a status of a sound processor of an auditory prosthesis, and selectively initiating autonomous programming of the sound processor based, at least in part, on the determined status of the sound processor.

17 Claims, 11 Drawing Sheets

(56) References Cited

U.S. PATENT DOCUMENTS

| | | |
|---|---|---|
| 2004/0024429 A1 | 2/2004 | Daly |
| 2006/0222194 A1 | 10/2006 | Bramslow et al. |
| 2007/0135862 A1 | 6/2007 | Nicolai et al. |
| 2009/0222064 A1 | 9/2009 | Faltys et al. |
| 2010/0106218 A1 | 4/2010 | Botros |
| 2014/0126731 A1 | 5/2014 | Litvak et al. |
| 2014/0376755 A1 | 12/2014 | Kang |
| 2016/0175593 A1* | 6/2016 | Macken ............ A61N 1/36038 607/57 |

FOREIGN PATENT DOCUMENTS

| | | |
|---|---|---|
| EP | 0197889 A1 | 10/1986 |
| EP | 1338301 A1 | 8/2003 |
| WO | WO 2006/022993 A2 | 3/2006 |
| WO | WO 2016/162758 | 10/2016 |

OTHER PUBLICATIONS

Office action received in Chinese Application No. 201980045717.9, dated Sep. 26, 2023, in 11 pages.
Office Action received in Chinese Application No. 201980045717.9, 12 pages, dated Mar. 21, 2024.

* cited by examiner

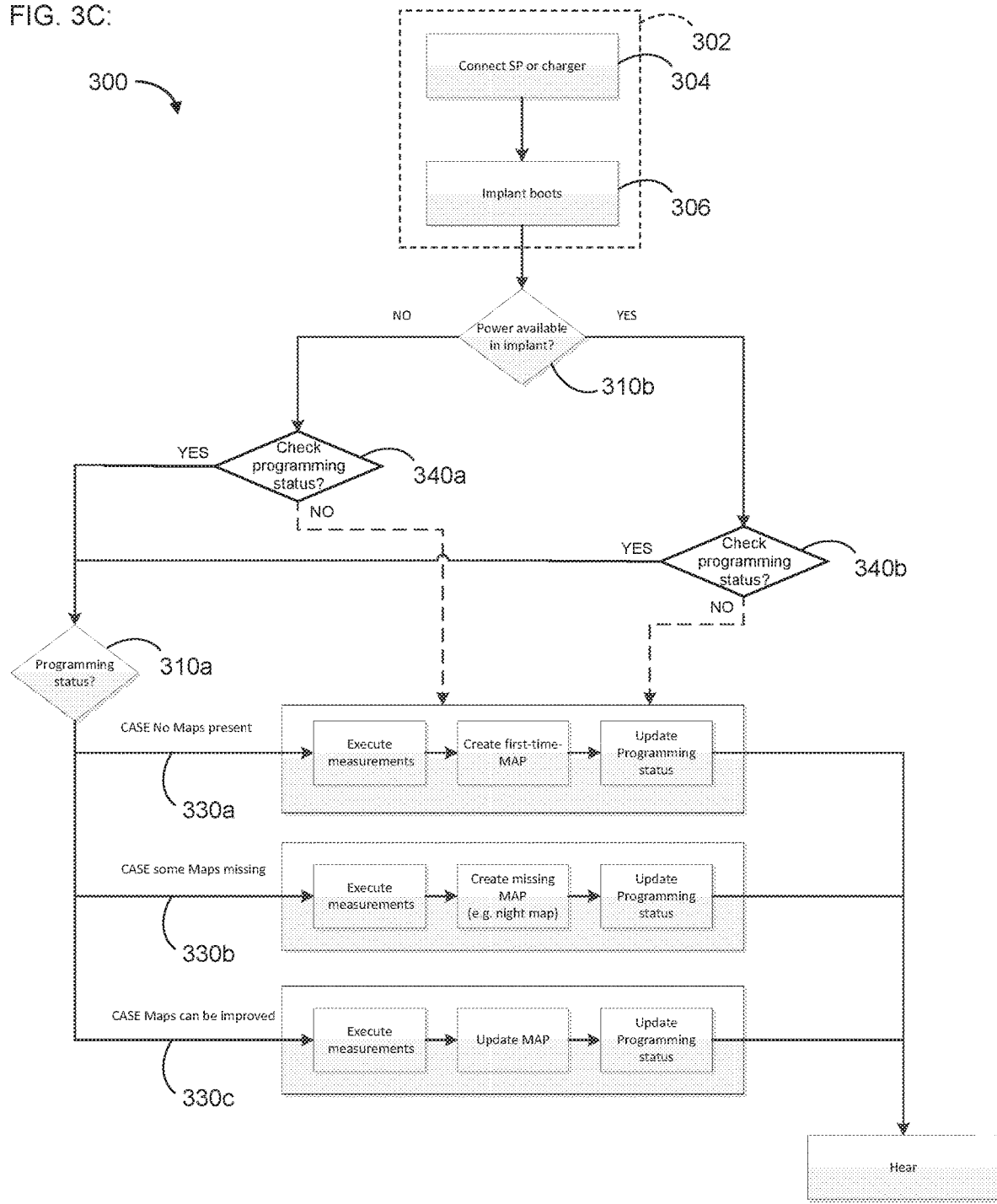

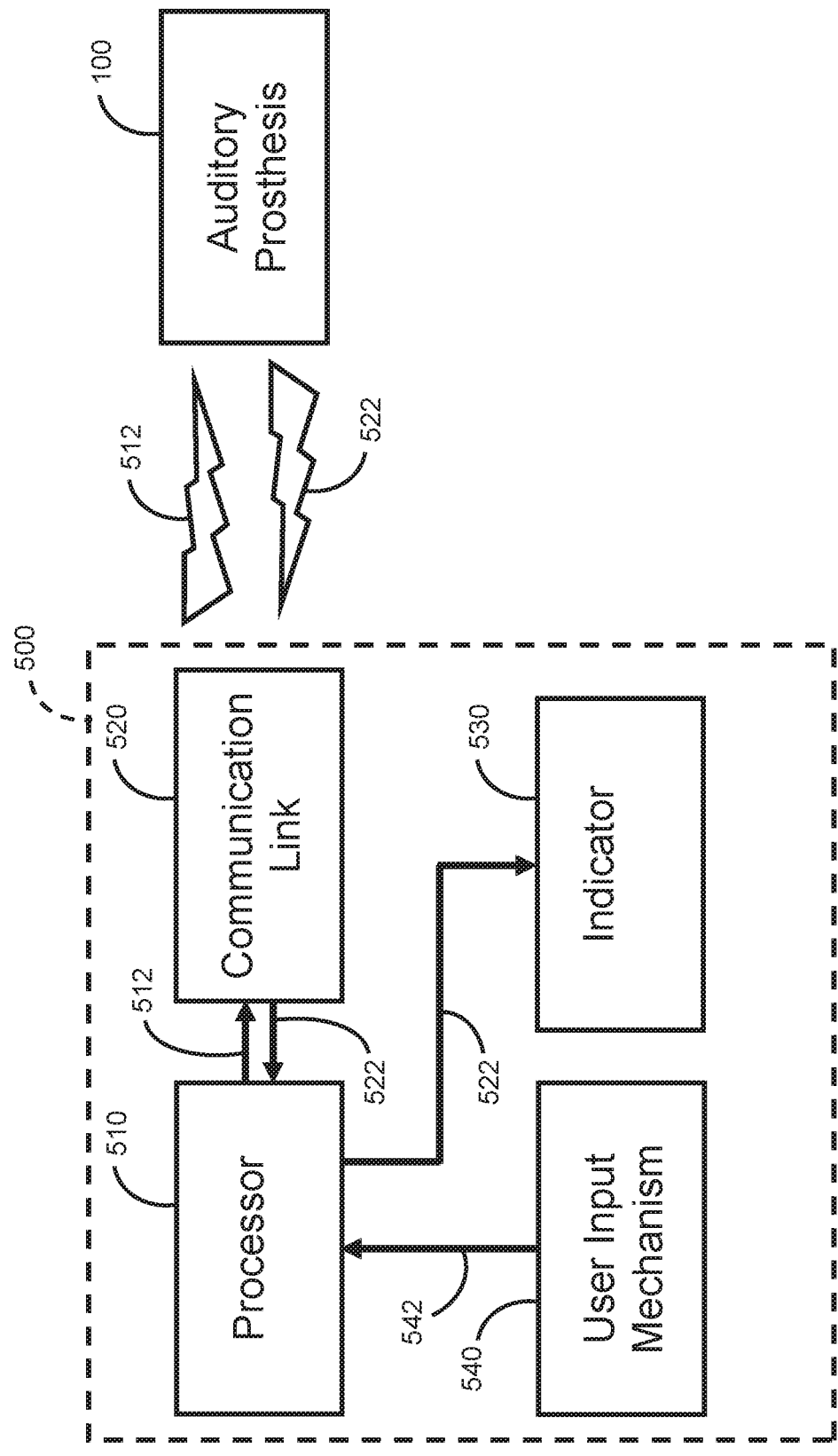

SYSTEM AND METHOD FOR AUTONOMOUSLY ENABLING AN AUDITORY PROSTHESIS

BACKGROUND

Field

The present application relates generally to implantable auditory prostheses, and more specifically systems and methods for enabling autonomous programming of the auditory prostheses.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. Auditory prostheses of various types are widely used to improve the lives of users. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Forms of these auditory prostheses which are "mostly implantable," "fully implantable," or "totally implantable" have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs"), mostly implantable cochlear implants ("MICI"), and fully implantable middle ear implants utilizing totally implantable actuators ("TIAs").

While conventional auditory prostheses use externally disposed microphone assemblies, certain mostly, fully, or totally implantable auditory prostheses use subcutaneously implantable microphone assemblies. Such microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region).

SUMMARY

In one aspect disclosed herein, a method is provided which comprises determining a status of a sound processor of an auditory prosthesis, and selectively initiating autonomous programming of the sound processor based, at least in part, on the determined status of the sound processor.

In another aspect disclosed herein, an apparatus is provided which comprises sound processing circuitry of an auditory prosthesis. The sound processing circuitry is configured to access one or more signal processing data sets, to use at least one of the accessed signal processing data sets to process signals received from a microphone of the auditory prosthesis, and to generate stimulation signals transmitted to at least a portion of the auditory system of a recipient of the auditory prosthesis. The apparatus further comprises data storage circuitry configured to store the one or more signal processing data sets. The apparatus further comprises control circuitry of the auditory prosthesis. The control circuitry is configured to access information indicative of at least one of: a programming status of the auditory prosthesis, an identification of the auditory prosthesis, and a power status of the auditory prosthesis. The control circuitry is further configured to selectively initiate, in response at least in part to the accessed information, autonomous programming of the auditory prosthesis to generate or modify at least one of the signal processing data sets.

In still another aspect disclosed herein, an apparatus is provided which comprises at least one processor configured to generate at least one control signal. The apparatus further comprises at least one communication link in operable communication with the at least one processor. The at least one communication link is configured to transmit the at least one control signal to an implanted auditory prosthesis and to receive at least one status signal from the implanted auditory prosthesis. The implanted auditory prosthesis comprises a sound processor configured to transmit the at least one status signal indicative of a status of the sound processor and to perform, in response to the at least one control signal, autonomous programming to generate or modify of at least one operational parameter map. The apparatus further comprises at least one indicator in operable communication with the at least one processor. The at least one indicator is configured to communicate, in response to the received at least one status signal, the status of the sound processor to at least one of a recipient of the implanted auditory prosthesis and a clinician. The apparatus further comprises at least one user input mechanism in operable communication with the at least one processor. The at least one user input mechanism is configured to be utilized by the at least one of the recipient and the clinician to provide at least one user input signal to the at least one processor. The at least one processor is configured to respond to the at least one user input signal by generating the at least one control signal.

In still another aspect disclosed herein, a method is provided which comprises initiating a self-programming operation by a sound processor of an implanted auditory prosthesis, and controlling the self-programming operation based at least in part on a determined status of the auditory prosthesis.

BRIEF DESCRIPTION OF THE DRAWINGS

Embodiments are described herein in conjunction with the accompanying drawings, in which:

FIG. 3C is a flow diagram of another example of the method in accordance with certain embodiments described herein;

FIG. 5 schematically illustrates an example apparatus in accordance with certain embodiments described herein.

DETAILED DESCRIPTION

Certain embodiments described herein provide a system and method for initiating a self-programming session of an auditory prosthesis based on a status of the auditory prosthesis. For example, the status can be that the auditory prosthesis is missing one or more operational parameter maps (e.g., because the auditory prosthesis has not been programmed or undergone a fitting procedure before) or that an identified one or more of the operational parameter maps warrants improvement. The auditory prosthesis of certain embodiments is configured to perform one or more self-programming sessions (e.g., utilizing neural response telemetry measurements) to generate a missing operational parameter map or to improve or modify an existing operational parameter map. Such self-programming sessions can produce operational parameter maps either during or soon after the implant surgery, thereby allowing the recipient to begin to enjoy the benefits of the auditory prosthesis immediately after waking from the implant surgery (e.g., "wake-up with hearing" or "wake up with sound"). In certain embodiments, the status of the auditory prosthesis with regard to the operational parameter maps and the self-programming is communicated to the clinician and/or recipient through an indicator.

The teachings detailed herein are applicable, in at least some embodiments, to any type of auditory prosthesis utilizing an implantable actuator assembly including but not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Embodiments can include any type of auditory prosthesis that can utilize the teachings detailed herein and/or variations thereof. In some embodiments, the teachings detailed herein and/or variations thereof can be utilized in other types of prostheses beyond auditory prostheses.

Figure 1:
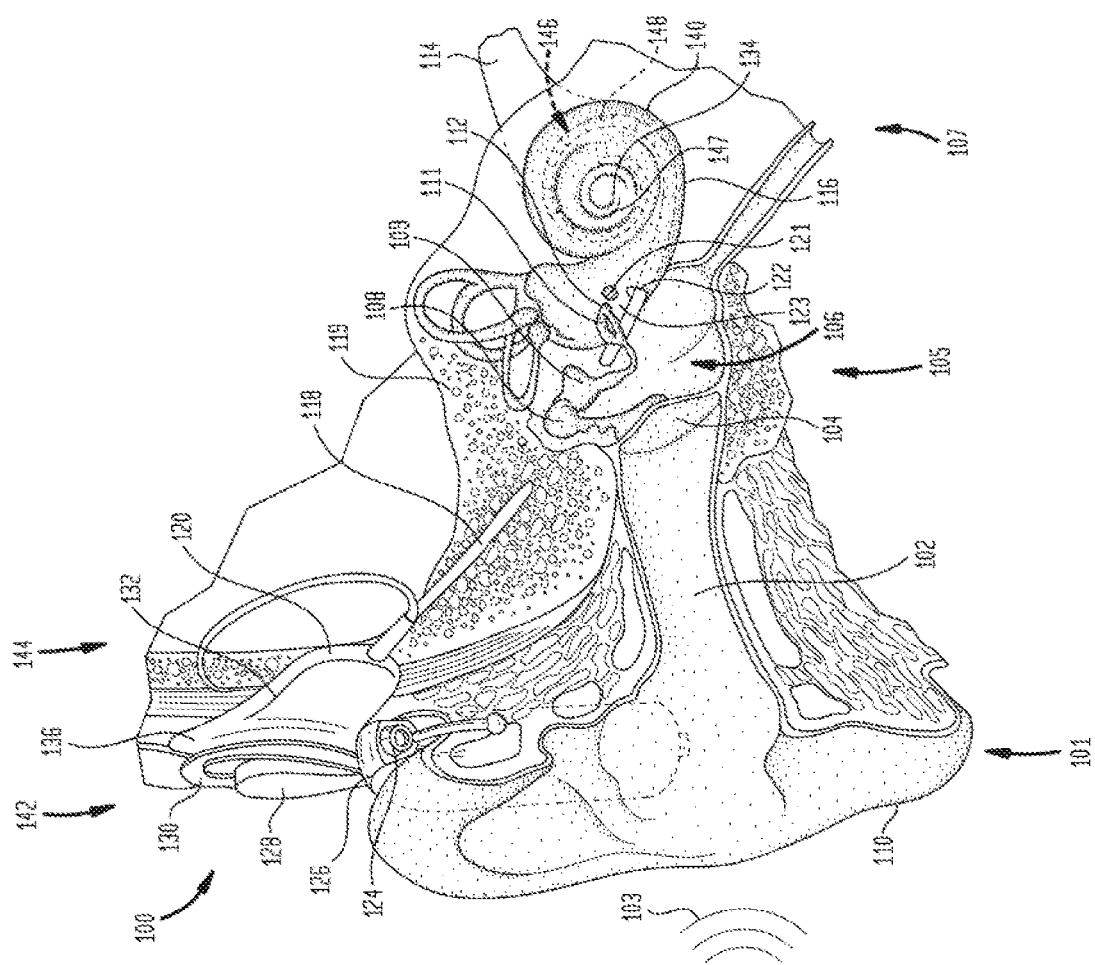
FIG. 1 is a perspective view of an example cochlear implant auditory prosthesis implanted in a recipient in accordance with certain embodiments described herein.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant; a mostly implantable cochlear implant) in accordance with certain embodiments described herein can replace the external microphone assembly 124 shown in FIG. 1 with a subcutaneously implantable assembly comprising an acoustic transducer (e.g., microphone).

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable).

As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other embodiments, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Proper operation of various implanted auditory prostheses (e.g., cochlear implant systems; acoustical implant systems) depends upon the establishment of one or more signal processing data sets (e.g., recipient-specific fitting parameters; operational parameter maps) that are utilized by the auditory prosthesis to generate proper, safe, and comfortable stimulation signals in response to received sound signals and which are fitted or customized to conform to the specific recipient demands. Typically, for cochlear implants, the one or more signal processing data sets are initially established by a fitting procedure during a visit by the recipient to a clinician. During the visit, the clinician performs a fitting procedure (e.g., initiating a number of beeps or tones and asking the recipient to judge loudness, over a number of stimulation or frequency channels. In some circumstances, instead of utilizing the beeps or tones, neural response telemetry ("NRT") can be used in a fitting procedure by making measurements of the response of the recipient's auditory nerve to electrical stimulation applied using the cochlear implant. For example, NRT can include providing stimulation signals to each stimulation channel (e.g., electrode of the electrode array) and measuring the neural response (e.g., electrically-evoked compound action potential) using another electrode of the electrode array (e.g., a neighboring electrode to the stimulating electrode). These measurements can include collection and determination of recipient-specific parameters such as threshold levels (T levels) and maximum comfort levels (C levels) for each stimulation channel. Subsequent visits and fitting procedures are performed to obtain further NRT measurements to further optimize the one or more signal processing data sets (e.g., C-level profiles and T-level profiles of the recipient).

There can be a significant time delay (e.g., days or weeks) between implantation of the cochlear implant and the initial fitting procedure during which the one or more signal processing data sets are established, and even further time delays (e.g., days or weeks) between the initial fitting procedure and subsequent fitting procedures during which the one or more signal processing data sets are further optimized. As a result, the recipient does not begin to enjoy the benefits provided by the cochlear implant until after the initial fitting procedure and does not fully enjoy the benefits provided by the cochlear implant until the one or more signal processing data sets are fully optimized.

Rather than relying on a clinician, autonomous programming (e.g., self-programming) of the auditory prosthesis 100 can be used to generate the initial values of the one or more signal processing data sets and/or subsequent optimization of the one or more signal processing data sets. As used herein, the term "autonomous programming" has its broadest reasonable interpretation, including but not limited to, automatically measuring an evoked neural response (e.g., by monitoring the recipient's auditory nerve and/or brain signals) and using such measurements to automatically generate and/or modify one or more signal processing data sets (see, e.g., U.S. Pat. No. 8,965,520) without the substantial involvement of a clinician (e.g., without clinical intervention beyond merely initiating the procedure).

Using autonomous programming in accordance with certain embodiments described herein, an auditory prosthesis can begin generating at least one signal processing data set soon after completion of the implantation of the auditory prosthesis in the recipient such that the at least one signal processing data set is usable by the auditory prosthesis by the time the recipient wakes up after the implant surgery, thereby enabling the recipient to wake up after the implant surgery with at least a preliminary level of hearing. Furthermore, in certain embodiments described herein, autonomous programming can be used by an auditory prosthesis having an autonomous power source (e.g., an implanted power source) to automatically create additional operational parameter maps tailored for use by the auditory prosthesis in certain environments and/or during certain times (e.g., during nighttime) and to improve one or more operational parameter maps without clinical intervention.

FIGS. 2A-2E schematically illustrate examples of an apparatus 200 in accordance with certain embodiments described herein. The apparatus 200 comprises sound processing circuitry 220 of an auditory prosthesis 100. The sound processing circuitry 220 is configured to access one or more signal processing data sets 232 and to use at least one of the accessed signal processing data sets 232 to process signals 212 received from a microphone 210 of the auditory prosthesis 100 and to generate stimulation signals 222 transmitted to at least a portion of the auditory system of a recipient of the auditory prosthesis 100. The apparatus 200 further comprises data storage circuitry 230 configured to store the one or more signal processing data sets 232. The apparatus 200 further comprises control circuitry 240 of the auditory prosthesis 100. The control circuitry 240 is configured to access information 250 indicative of at least one of: a programming status of the auditory prosthesis 100, an identification of the auditory prosthesis 100, and a power status of the auditory prosthesis 100. The control circuitry 240 is further configured to selectively initiate, in response at least in part to the accessed information 250, autonomous programming of the auditory prosthesis 100 to generate or modify at least one of the signal processing data sets 232.

In certain embodiments, the microphone 210 comprises an external microphone assembly 124 (see, e.g., FIG. 1), while in certain other embodiments, the microphone 210 comprises a subcutaneously implantable microphone assembly. The microphone 210 of certain embodiments comprises an acoustic transducer configured to convert received sound signals into electrical signals 212 and to transmit the signals 212 to the sound processing circuitry 220. In certain embodiments, the microphone 210 wirelessly transmits the signals 212 to the sound processing circuitry 220, while in certain other embodiments, the microphone 210 is wired to the sound processing circuitry 220 and transmits the signals 212 to the sound processing circuitry 220 via the wires.

The sound processing circuitry 220 of certain embodiments comprises at least one processor (e.g., microelectronic circuitry; a sound processor) that can be located within a device external to the recipient's body or implanted within or on the recipient's body in operable communication with the data storage circuitry 230. In the example apparatus 200 of FIG. 2B, the sound processing circuitry 220 comprises a digital signal processor 224 and a stimulator unit 120. The digital signal processor 224 of certain embodiments comprises at least one integrated circuit configured to receive the signals 212 from the microphone 210 and to process the signals 212 (e.g., apply one or more of digitization, shifting, shaping, amplification, compression, filtering, and/or other signal conditioning to the signals 212). The digital signal processor 224 is further configured to transmit the processed signals to the stimulator unit 120. The stimulator unit 120 of certain embodiments is configured to respond to the processed signals from the digital signal processor 224 and to generate and transmit the stimulation signals 222 to a portion of the auditory system of the recipient (e.g., the cochlea 140) via the electrodes 148 of the electrode array 146, thereby stimulating the auditory nerve 114.

Figure 2A:
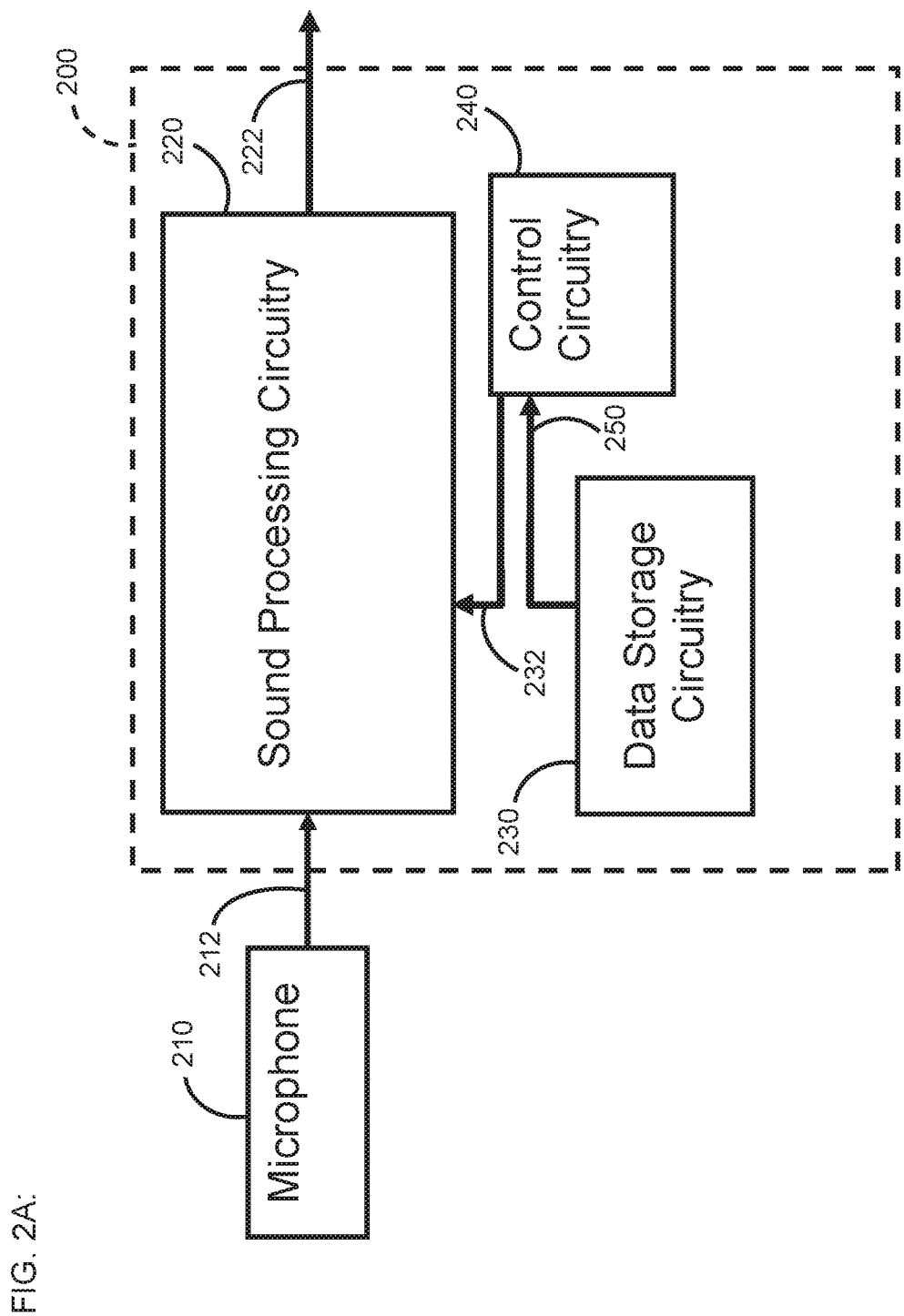
FIGS. 2A-2E schematically illustrate examples of an apparatus in accordance with certain embodiments described herein.
Figure 2B:
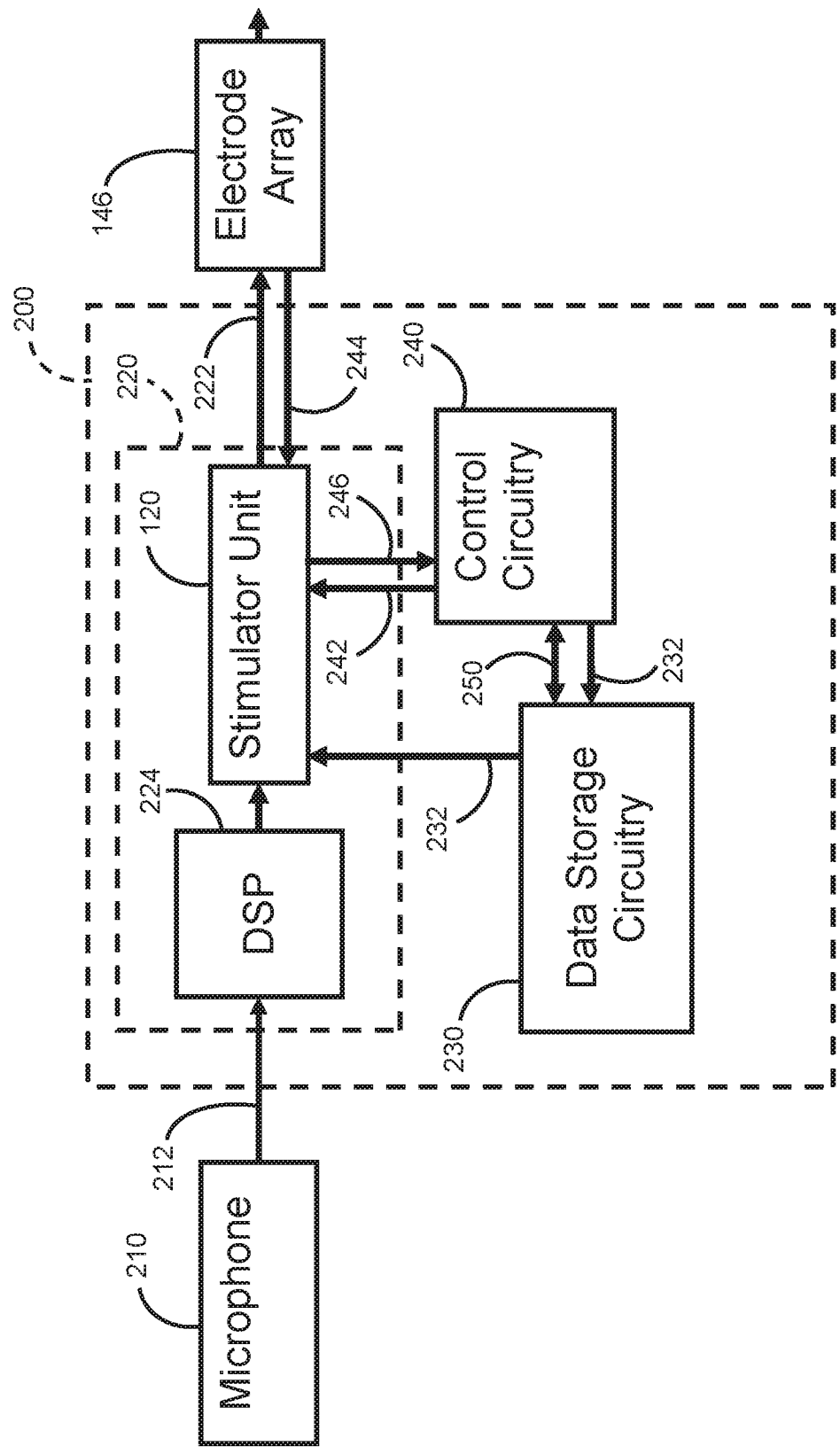

As schematically illustrated in FIG. 2B, the stimulator unit 120 of certain embodiments is configured to receive the one or more signal processing data sets 232 (e.g., sets of recipient-specific fitting parameters; sets of operational parameter maps) from the data storage circuitry 230 and to generate the stimulation signals 222 based at least in part on the one or more signal processing data sets 232. While FIG. 2B schematically illustrates the stimulator unit 120 receiving the one or more signal processing data sets 232 directly from the data storage circuitry 232 and the digital signal processor 224 and the stimulator unit 120 as separate components of the sound processing circuitry 220, other configurations are also compatible with certain embodiments described herein (e.g., the digital signal processor 224 receiving the one or more signal processing data sets 232 directly from the data storage circuitry 230; the digital signal processor 224 or the stimulation unit 120 receiving the one or more signal processing data sets 232 directly from the control circuitry 240; the stimulator unit 120 being a separate component from the sound processing circuitry 220).

In certain embodiments, the data storage circuitry 230 comprises non-volatile memory (e.g., flash memory) circuitry in operable communication with the sound processing circuitry 220 and the control circuitry 240. As described herein, the data storage circuitry 230 is configured to receive one or more signal processing data sets 232 from the control circuitry 240, to store the one or more signal processing data sets 232, and to provide the one or more signal processing data sets 232 to the sound processing circuitry 220.

In certain embodiments, the control circuitry 240 comprises at least one processor (e.g., microelectronic circuitry) in operable communication with the sound processing circuitry 220 and with the data storage circuitry 230. In certain embodiments (see, e.g., FIG. 2B), the control circuitry 240 is configured to conduct autonomous programming of the apparatus 200 by transmitting control signals 242 to the stimulator unit 120, which is configured to respond to the control signals 242 by performing neural response telemetry measurements to be used in the autonomous programming. For example, in response to the control signals 242, the stimulator unit 120 can generate stimulation signals 222 and can transmit the stimulation signals 222 to at least one electrode 148 of the electrode array 146 to evoke a neural response from the recipient's auditory system. In response to the stimulation signals 222, the recipient's auditory system generates electrical signals 244, which the stimulator unit 120 detects using at least some of the other electrodes 148 of the electrode array 146. The stimulator unit 120 is further configured to transmit signals 246 indicative of the measured response to the control circuitry 240. Using the measured response of the recipient's auditory system (e.g., as expressed by the signals 246), the control circuitry 240 of certain embodiments generates or modifies at least one of the signal processing data sets 232.

In certain embodiments, the control circuitry 240 is configured to access information 250 indicative of at least one aspect of the auditory prosthesis 100 and to selectively initiate autonomous programming of the auditory prosthesis 100 in response at least in part to the accessed information 250. As schematically illustrated by FIG. 2B, in certain embodiments, the data storage circuitry 230 is configured to store the signal processing data sets 232 and the information 250, and the control circuitry 240 is configured to access the information 250 from the data storage circuitry 230. The information 250 of certain embodiments is indicative of a programming status of the auditory prosthesis 100 (e.g., indicative of whether the auditory prosthesis 100 had been previously programmed to include one or more of the signal processing data sets 232; indicative of one or more statuses of the one or more signal processing data sets 232; indicative of whether a signal processing data set 232 is stored in the data storage circuitry 230; indicative of whether a signal processing data set 232 warrants improvement using autonomous programming).

Upon accessing information 250 indicative of at least one of the signal processing data sets 232 being unavailable (e.g., not stored in the data storage circuitry 230) or warranting improvement, the control circuitry 240 can initiate autonomous programming to generate the previously unavailable signal processing data set 232 or to modify (e.g., improve) the signal processing data set 232 that warranted improvement. Besides storing the newly generated or newly improved signal processing data set 232 in the data storage circuitry 230, the control circuitry 240 of certain embodiments further updates the information 250 stored by the data storage circuitry 250 to reflect the updated status of the signal processing data set 232. For example, the data storage circuitry 230 can comprise one or more bytes (e.g., in a predetermined storage location) configured to be read by the control circuitry 240 to determine the programming status and further configured to be written to by the control circuitry 240 to update the programming status once the at least one of the signal processing data sets 232 is generated or modified. In certain such embodiments, a predetermined value can be written into the one or more bytes during manufacturing of the apparatus 200, and this predetermined value can be interpreted by the control circuitry 240 as indicating that a corresponding signal processing data set 232 is missing (e.g., no mapping procedures have yet been performed using the apparatus 200 since it left manufacturing). In certain other embodiments, a predetermined value can be written into the one or more bytes during or immediately after a mapping procedure has been performed using the apparatus 200 to generate the corresponding signal processing data set 232, and the absence of this predetermined value can be interpreted by the control circuitry as indicating that the signal processing data set 232 is missing (e.g., no mapping procedures have yet been performed using the apparatus 200 since it left manufacturing). In certain embodiments, the predetermined value can be indicative of a corresponding signal processing data set 232 (e.g., an identification number of the signal processing data set 232), while in certain other embodiments, the predetermined value is not indicative of a corresponding signal processing data set 232.

Figure 2C:
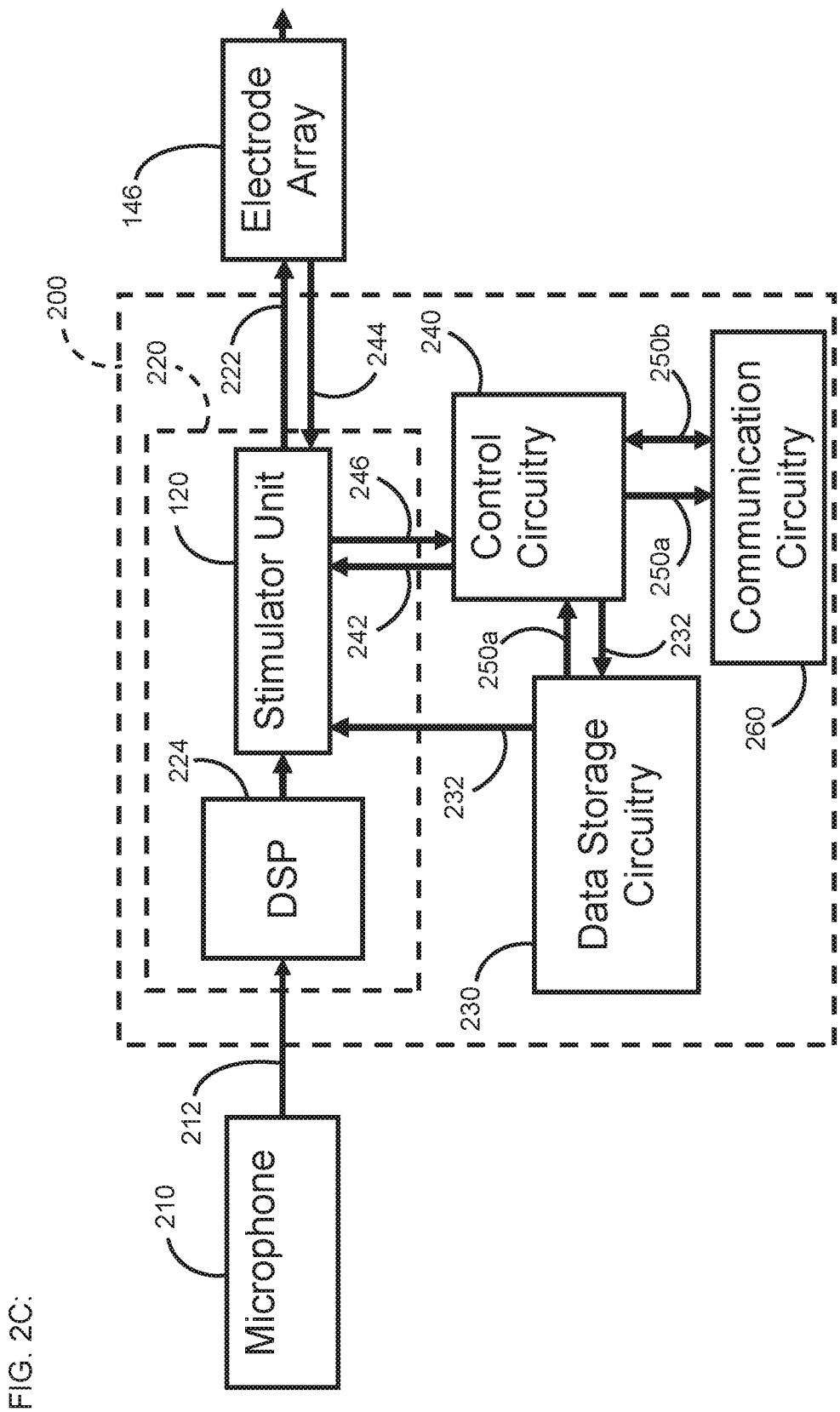

In certain other embodiments, the information 250 stored in the data storage circuitry 230 comprises an identification 250a of the auditory prosthesis 100 (e.g., a unique serial number indicative of the identification) and the information 250b indicative of the programming status of the auditory prosthesis 100 is stored remotely from the apparatus 200 (e.g., on a dedicated server available via wireless communication with the internet). As schematically illustrated by FIG. 2C, in certain such embodiments, the apparatus 200 comprises communication circuitry 260 (e.g., wireless; radio-frequency; Bluetooth; WiFi) in operable communication with the control circuitry 240 and configured to be used by the control circuitry 240 to access the information 250b indicative of the programming status of the auditory prosthesis 100. For example, the control circuitry 240 can access the identification 250a of the auditory prosthesis 100 from the data storage circuitry 230, transmit the identification 250a via the communication circuitry 260 to the server along with a request for the programming status 250b of the auditory prosthesis 100 corresponding to the identification 250a, and receive the programming status 250b of the auditory prosthesis 100 from the server via the communication circuitry 260. After generating and/or modifying a signal processing data set 232, the control circuitry 240 can also transmit the identification 250a and the information 250b indicative of the updated programming status to be stored on the server to reflect the updated status of the signal processing data set 232 for the auditory prosthesis 100 identified by the identification 250a.

In certain embodiments, the control circuitry 240 is configured to utilize the communication circuitry 260 to access (e.g., retrieve; modify; store) one or more signal processing data sets 232 that are stored remotely from the apparatus 200 (e.g., on a dedicated server available via wireless communication with the internet; "in the cloud"). Besides the remotely stored signal processing data sets 232, certain embodiments can also remotely store impedances, NRT values, and/or diagnostic information in a database dedicated to the particular auditory prosthesis 100. In certain embodiments, the database can be accessed by an artificial intelligence ("AI") software system to create and/or improve the signal processing data sets 232.

The remotely stored one or more signal processing data sets 232 are accessible by the apparatus 200. For example, an initial version of a signal processing data set 232 can be remotely stored but accessible to the apparatus 200 via the communication circuitry 260, and the apparatus 200 can be configured to subsequently modify the initial version to create a version tailored to the recipient. For another example, the apparatus 200 can be configured to upload one or more signal processing data sets 232 to a remote storage location as backup copies to the one or more signal processing data sets 232 locally stored in the data storage circuitry 230. In certain embodiments, the accessing of the one or more signal processing data sets 232 by the control circuitry 240 can be performed in response to the status (e.g., programming status and/or power status) of the apparatus 200. For still another example, by having one or more recipient-tailored signal processing data sets 232 stored remotely from the apparatus 200, a new apparatus 200 that has not previously been used with the implanted acoustic prosthesis 100 of the recipient can be placed on the recipient and can access the remotely-stored recipient-tailored signal processing data sets 232 to provide hearing to the recipient.

Figure 2D:
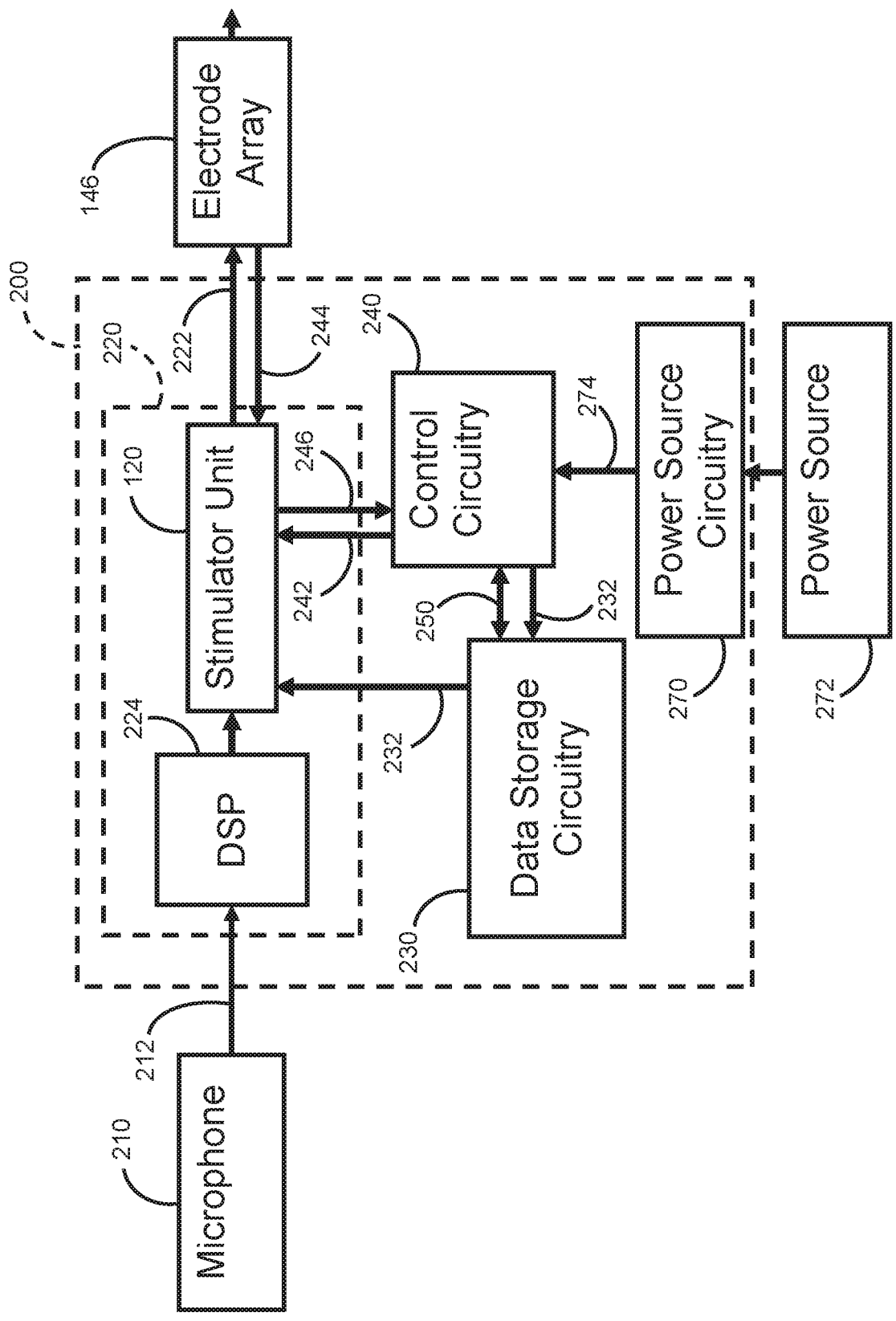

In certain embodiments, as schematically illustrated by FIG. 2D, the apparatus 200 comprises power source circuitry 270 (e.g., at least one processor; microelectronic circuitry) configured to be in operable communication with the control circuitry 240 and with a power source 272 (e.g., battery) of the auditory prosthesis 100. For example, the power source circuitry 270 can be configured to detect whether the apparatus 200 is in a first power status in which the apparatus 200 is configured to receive power from an internal power source (e.g., a power source implanted within or on the recipient) that is continually operationally coupled to the apparatus 200 or in a second power status in which the apparatus 200 is configured to receive power from an external power source (e.g., a power source external to the recipient) that is selectively operationally coupled to the apparatus 200. The power source circuitry 270 can be further configured to provide the control circuitry 240 with a power status signal 274 of the auditory prosthesis 100 indicative of the power status of the apparatus 200.

The control circuitry 240 of certain embodiments is configured to initiate and/or direct the autonomous programming procedure in response to the power status signal 274 detected by interrogating the power source circuitry 270. For example, when the power status signal 274 is indicative of the first power status, the control circuitry 240 can selectively initiate autonomous programming regardless of whether the apparatus 200 is operatively coupled to an external power source. In this way, certain embodiments can perform autonomous programming at any time since the apparatus 200 is self-powered. In certain embodiments with a self-powered apparatus 200, the NRT measurements used to create or improve the signal processing data sets 232 can be executed over a long time, thereby enabling (e.g., through averaging) the establishment of very precise signal processing data sets 232, thereby improving the quality of these signal processing data sets 232. Furthermore, in certain embodiments utilizing a self-powered apparatus 200, the NRT measurements can be made while the recipient remains asleep after the implant surgery, thereby allowing the recipient to wake up after surgery with hearing already restored.

For another example, when the power status signal 274 is indicative of the second power status, the control circuitry 240 can selectively initiate autonomous programming only when the apparatus 200 is operatively coupled to the external power source. In certain embodiments, the power status signal 274 from the power source circuitry 270 is indicative of a status of the power transfer (e.g., a measurement of an electrical voltage and/or current) from the power source 272 to the auditory prosthesis 100, and the control circuitry 240 is configured to selectively initiate the autonomous programming based on the status of the power transfer (e.g., whether the measured electrical voltage and/or current is above a predetermined threshold corresponding to sufficient power for such autonomous programming). In certain embodiments utilizing an externally powered apparatus 200, the NRT measurements can be made once the power source is in operative communication with the apparatus 200. If this connection is made either during the implant surgery or while the recipient remains asleep after the implant surgery, with sufficient time to create a signal processing data set 2332, the recipient can wake up after surgery with hearing already restored.

Figure 2E:
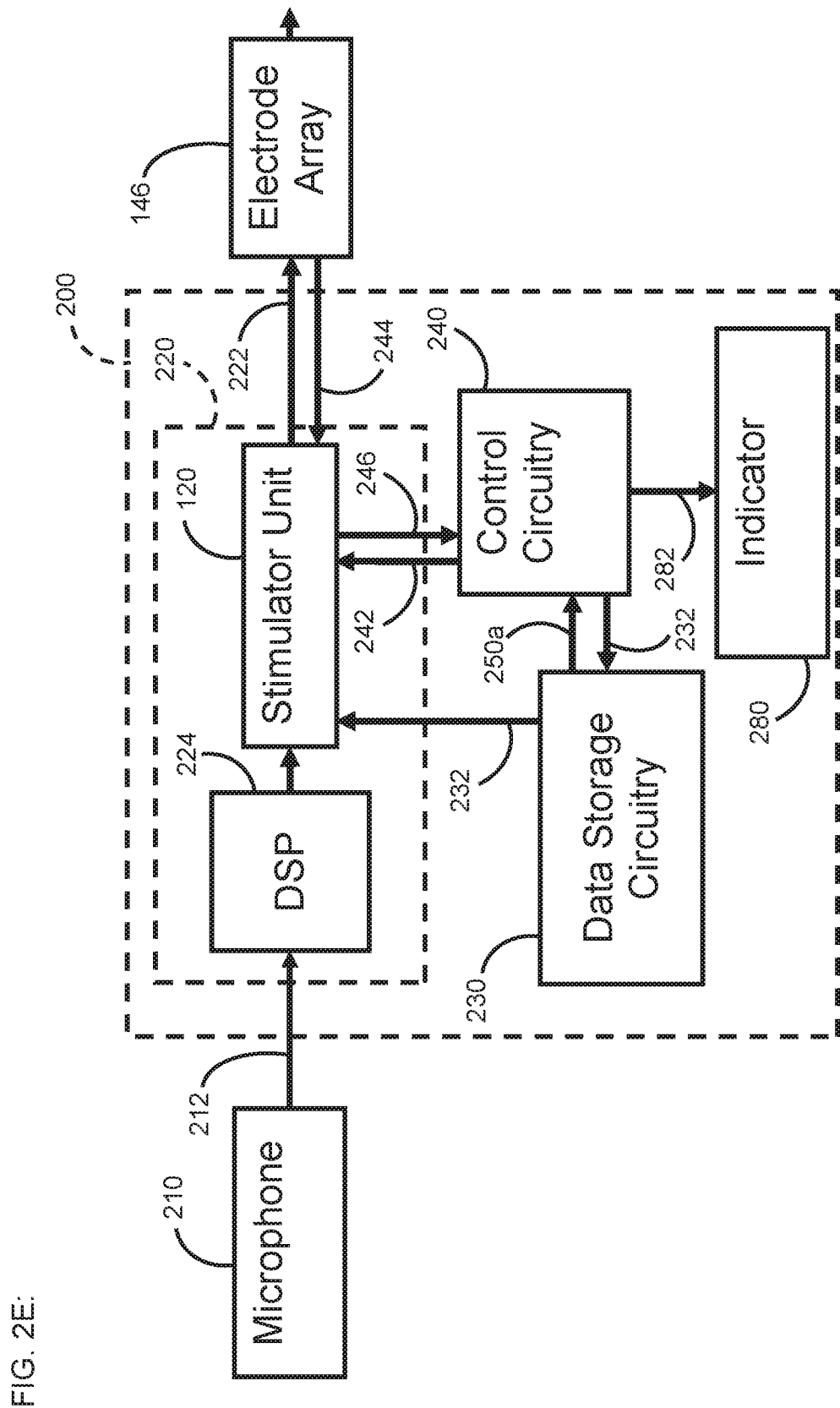

In certain embodiments, as schematically illustrated by FIG. 2E, the apparatus 200 comprises at least one indicator 280 (e.g., a display; an LED or other light source; a speaker) in operative communication with the control circuitry 240. In response to signals 282 from the control circuitry 240, the at least one indicator 280 is configured to indicate to the recipient and/or clinician (e.g., via an image, color, sound, or other signal perceptible by the recipient and/or clinician) a status of the apparatus 200 with regard to autonomous programming. For example, the status can comprise at least one of: whether the autonomous programming is currently being performed; whether the autonomous programming is currently encountering one or more problem conditions preventing proper operation of the autonomous programming; which of the one or more signal processing data sets 232 is being generated or modified by the autonomous programming; completion of the autonomous programming. In certain embodiments, the control circuitry 240 is configured to respond to the detection of one or more problem conditions by entering a diagnostic mode in which the control circuitry 240 is configured to facilitate identifying and/or solving the problem conditions (e.g., by presenting information to the clinician for diagnosing the problem).

Figure 3A:
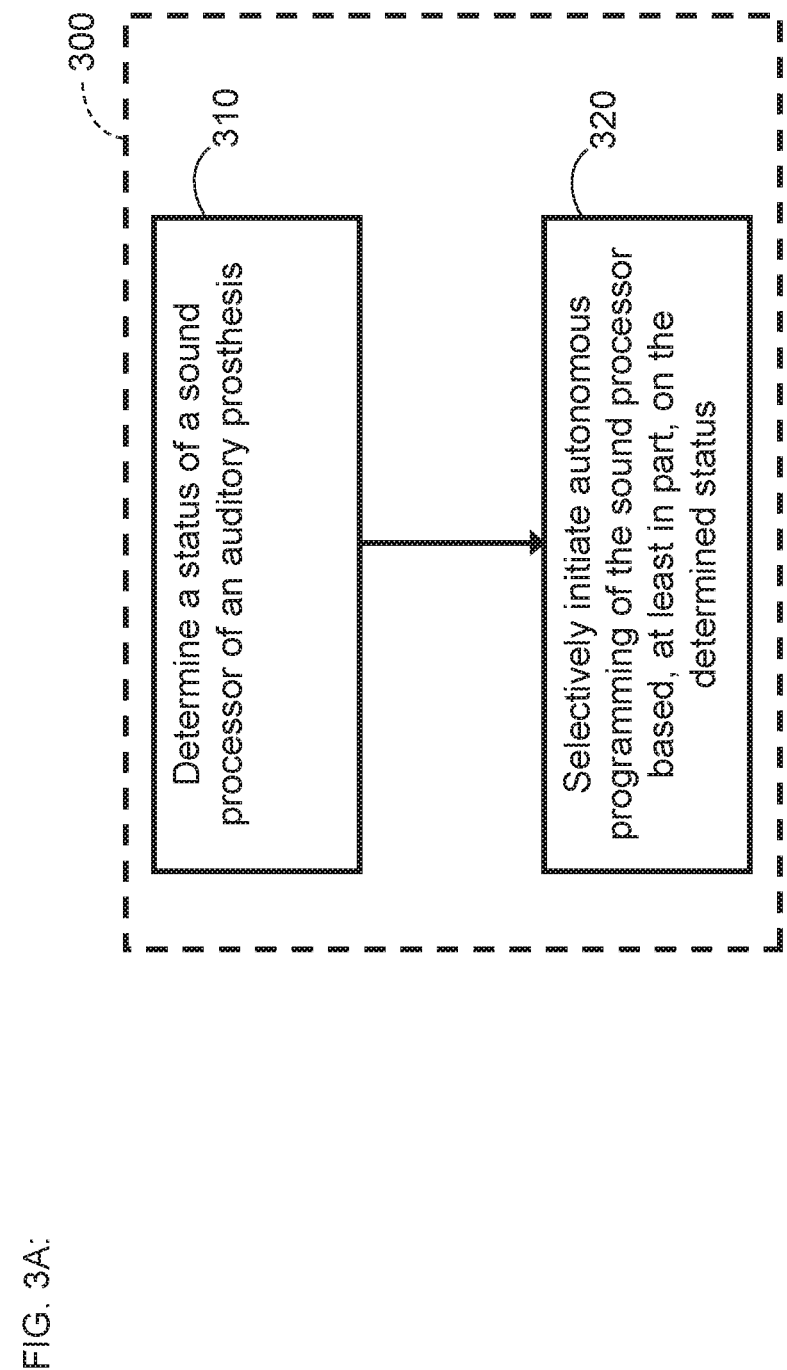
FIG. 3A is a flow diagram of an example of a method in accordance with certain embodiments described herein.

FIG. 3A is a flow diagram of an example of a method 300 in accordance with certain embodiments described herein. In an operational block 310, the method 300 comprises determining a status of a sound processor (e.g., sound processing circuitry 220; apparatus 200) of an auditory prosthesis 100. In an operational block 320, the method 300 further comprises selectively initiated autonomous programming of the sound processor based, at least in part, on the determined status of the sound processor.

In certain embodiments, the sound processor is configured to access one or more operational parameter maps (e.g., one or more signal processing data sets 232; one or more recipient-specific fitting parameters). The one or more operational parameter maps can comprise one or more of a plurality of operational parameter maps. For example, a first operational parameter map can be configured to be used by the sound processor in normal sound environments (e.g., during daytime; within a predetermined time period during which the recipient is expected to be awake; in environments with sound levels within a predetermined range). The first operational parameter map can be a default map (e.g., comprising normative data) to be used when the conditions and/or environments of the other operational parameter maps do not currently exist. A second operational parameter map can be configured to be used by the sound processor in quiet sound environments (e.g., in environments with sound levels below a predetermined threshold). A third operational parameter map can be configured to be used by the sound processor in noisy sound environments (e.g., in environments with sound levels above a predetermined threshold). A fourth operational parameter map can be configured to be used by the sound processor in musical sound environments (e.g., in environments in which the recipient is listening to music). A fifth operational parameter map can be configured to be used by the sound processor during sleep of the recipient (e.g., during nighttime; within a predetermined time period during which the recipient is expected to be asleep). Other operational parameter maps and other numbers of operational parameter maps are also compatible with certain embodiments described herein.

In certain embodiments, the sound processor is configured to be in one of a plurality of programming statuses. In a first programming status 330*a* of the sound processor, all of the one or more operational parameter maps are unavailable to the sound processor. For example, the sound processor can be in the first programming status 330*a* when the sound processor has not undergone any programming, autonomous or not, so there are no available operational parameter maps (e.g., no operational parameter maps in the data storage circuitry 230 of the apparatus 200). In a second programming status 330*b* of the sound processor, at least one but less than all of the operational parameter maps is unavailable to the sound processor. For example, the sound processor can be in the second programming status 330*b* when the sound processor has undergone at least some programming (e.g., autonomous; non-autonomous) such that some of the operational parameter maps are available to the sound processor (e.g., is in the data storage circuitry 230 of the apparatus 200) and at least one of the operational parameter maps is not available to the sound processor (e.g., is not in the data storage circuitry 230 of the apparatus 200). In a third programming status 330c of the sound processor, none of the operational parameter maps are unavailable to the sound processor. For example, the sound processor can be in the third programming status 330c when the sound processor has undergone sufficient programming (e.g., autonomous; non-autonomous) such that all of the operational parameter maps are available to the sound processor (e.g., are in the data storage circuitry 230 of the apparatus 200).

Figure 3B:
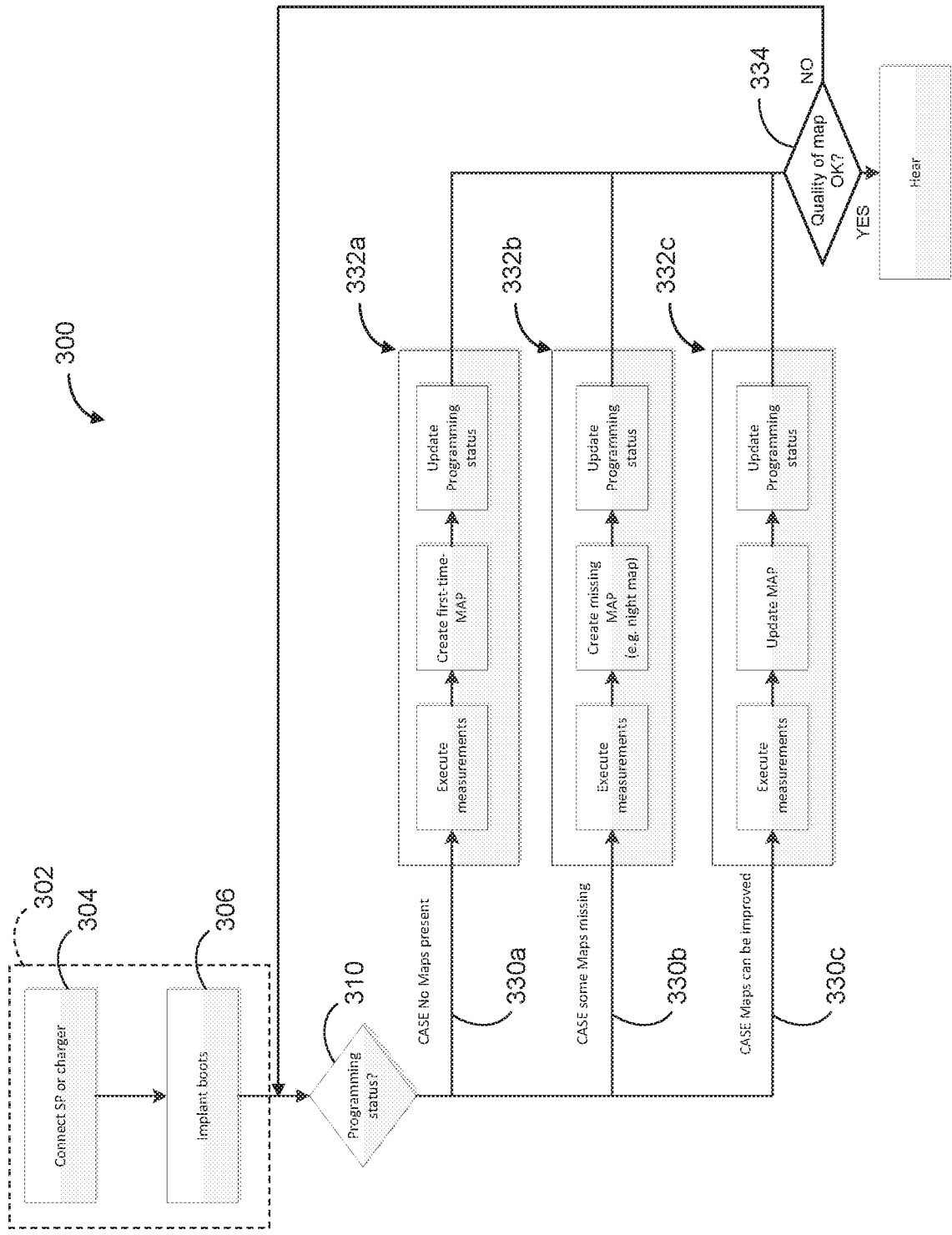
FIG. 3B is a flow diagram of another example of the method in accordance with certain embodiments described herein.

FIG. 3B is a flow diagram of another example of the method 300 in accordance with certain embodiments described herein. As shown in FIG. 3B, the method 300 of certain embodiments comprises an operational block 302 in which certain initial actions are performed (e.g., placing an external sound processor and/or an external power source or charger on the recipient to be in operative communication with the implanted portion of the auditory prosthesis 100 in an operational block 304; powering up or "booting" the auditory prosthesis 100 in an operational block 306). In certain embodiments, one or more of these initial actions is performed at the time of implantation (e.g., for a totally implanted cochlear implant system in which the sound processor and power source are implanted while in operative communication with the other components of the system).

As shown in FIG. 3B, determining the status of the sound processor in the operational block 310 directs the method 300 into one of a plurality of alternative logical paths 332a, 332b, 332c. When the programming status is the first programming status 330a, the method 300 further comprises the logical path 332a comprising using autonomous programming to generate at least one of the unavailable operational parameter maps (e.g., executing NRT measurements and creating a "first-time" map) and updating the programming status of the sound processor (e.g., updating the information 250 to be subsequently accessed in future determinations of the status). When the programming status is in the second programming status 330b, the method 300 further comprises the logical path 332b comprising determining which of the operational parameter maps is unavailable to the sound processor, and using the autonomous programming to generate at least one of the unavailable operational parameter maps (e.g., executing NRT measurements and creating a missing map), and updating the programming status of the sound processor. When the programming status is in the third programming status 330c, the method 300 further comprises the logical path 332c comprising determining whether any of the operational parameter maps warrants improvement by autonomous programming, using the autonomous programming to improve the operational parameter map warranting improvement (e.g., executing NRT measurements and updating the map), and updating the programming status of the sound processor. For example, besides denoting the availability or non-availability of each of the operational parameter maps, the status of the sound processor can further denote whether each of the available operational parameter maps warrants improvement (e.g., based on an amount of time since the previous update of the operational parameter map; based on the amount of data compiled and used in generating the operational parameter map).

While the logical paths 332a and 332b can be performed in a relatively short amount of time (e.g., a few minutes), the amount of time for the logical path 332c can depend on how much improvement is to be performed. After each of the logical paths 332a, 332b, 332c, the method 300 of certain embodiments further comprises, in an operational block 334, evaluating a quality of the operational parameter map that was generated or modified by the logical path 332a, 332b, 332c (e.g., based on an amount of data compiled and used in generating the operational parameter map). If the quality is below a predetermined threshold, the method 300 can comprise returning to the operational block 310 and performing additional autonomous programming in response to the status of the apparatus 200.

FIG. 3C is a flow diagram of another example of the method 300 in accordance with certain embodiments described herein. As shown in FIG. 3C, in certain embodiments determining the status of the sound processor comprises determining a programming status of the sound processor in an operational block 310a and further comprises determining a power status of the sound processor in an operational block 310b. For example, the sound processor can be in one of a plurality of power statuses. In a first power status, the sound processor is configured to receive power from an internal power source configured to be continually operationally coupled to the sound processor. In a second power status, the sound processor is configured to receive power from an external power source configured to be selectively operationally coupled to the sound processor. As shown in FIG. 3C, in certain embodiments, after determining the power status of the sound processor, the method 300 can include the option of bypassing the determination of the programming status of the sound processor.

When the power status is the second power status, selectively initiating autonomous programming is performed only when the sound processor is operatively coupled to the external power source. Since the sound processor in the second power status receives power from an external power source, the NRT measurements to be made as part of the autonomous programming are to be made only when the external power source is connected. When the power status is the first power status, selectively initiating autonomous programming is performed regardless of whether the sound processor is operatively coupled to the external power source. Since the sound processor in the first power status receives power from an internal power source, the NRT measurements to be made as part of the autonomous programming are made even if the sound processor is not connected to any external power source. As a result, the sound processor in the first power status is able to execute and/or average the NRT measurements over longer time periods, advantageously resulting in more improved operational parameter maps (e.g., maps that are very precise and have higher optimization) than maps generated using measurements over shorter time periods.

Figure 4:
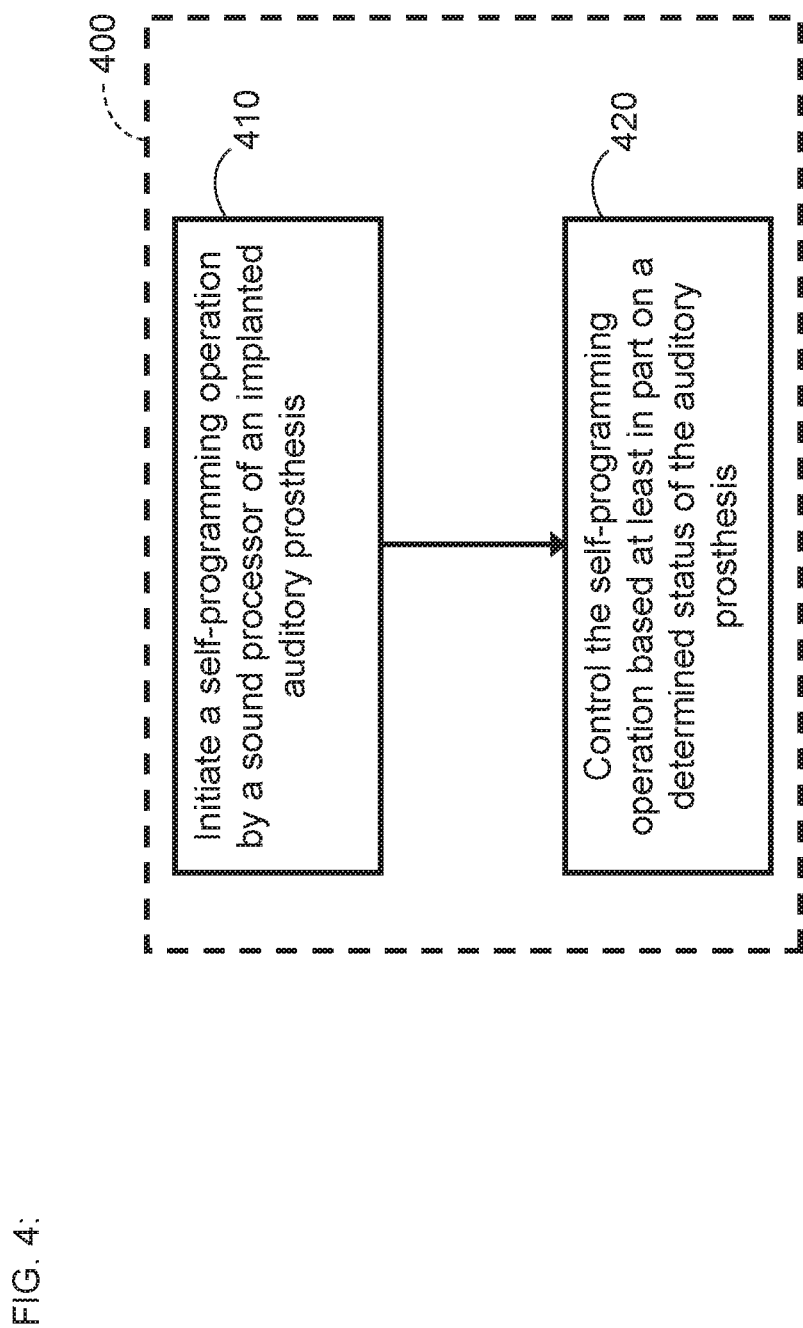
FIG. 4 is a flow diagram of an example method in accordance with certain embodiments described herein.

FIG. 4 is a flow diagram of an example method 400 in accordance with certain embodiments described herein. In an operational block 410, the method 400 comprises initiating a self-programming operation (e.g., autonomous programming) by a sound processor (e.g., sound processing circuitry 220; apparatus 200) of an implanted auditory prosthesis 100 (e.g., a cochlear implant system). In an operational block 420, the method 400 further comprises controlling the self-programming operation based at least in part on a determined status of the auditory prosthesis. For example, the determined status of the auditory prosthesis can comprise at least one of: a programming status of the auditory prosthesis and a power status of the auditory prosthesis. Controlling the self-programming operation in certain embodiments comprises directing the self-programming operation to generate or modify at least one operational parameter map of the auditory prosthesis.

FIG. 5 schematically illustrates an example apparatus 500 in accordance with certain embodiments described herein. In certain embodiments, the apparatus 500 comprises an external sound processor configured to be in operative communication with an implanted portion of the auditory prosthesis 100, while in certain other embodiments, the apparatus 500 comprises a separate external device (e.g., smart device; smartphone; tablet; remote control) configured to be in operative communication with an implanted portion of the auditory prosthesis 100, which can include an implanted sound processor.

In certain embodiments, the apparatus 500 comprises at least one processor 510 (e.g., microprocessor; microelectronic circuitry) configured to generate at least one control signal 512. The apparatus 500 further comprises at least one communication link 520 (e.g., wired; wireless; radio-frequency; Bluetooth; WiFi; inductive) in operable communication with the at least one processor 510. The at least one communication link 520 is configured to transmit the at least one control signal 512 to an implanted auditory prosthesis 100 and to receive at least one status signal 522 from the implanted auditory prosthesis 100. The implanted auditory prosthesis 100 comprises a sound processor (e.g., sound processing circuitry 220; apparatus 200) configured to transmit the at least one status signal 522 indicative of a status of the sound processor and to perform, in response to the at least one control signal 512, autonomous programming to generate or modify at least one operational parameter map. The apparatus 500 further comprises at least one indicator 530 (e.g., a display; an LED or other light source; a speaker) in operable communication with the at least one processor 510. The at least one indicator 530 is configured to communicate (e.g., via an image, color, sound, or other signal perceptible by the recipient and/or clinician), in response to the received at least one status signal 522, the status of the sound processor to at least one of a recipient of the implanted auditory prosthesis 100 and a clinician. The apparatus 500 further comprises at least one user input mechanisms 540 (e.g., button; switch; touchpad; trackball; mouse) in operable communication with the at least one processor 510. The at least one user input mechanism 540 is configured to be utilized by the at least one of the recipient and the clinician to provide at least one user input signal 542 to the at least one processor 510, and the at least one processor 510 is configured to respond to the at least one user input signal 542 by generating the at least one control signal 512.

In certain embodiments, the apparatus 500 can be used to initiate the method 300 and/or the method 400 and can be used in conjunction with the apparatus 200 of the auditory prosthesis 100. For example, during or soon after the implant surgery (e.g., in the operating theatre), a clinician can access the user input mechanism 540 to instruct the apparatus 500 to communicate a first control signal 512a to the auditory prosthesis 100, the first control signal 512a configured to instruct the auditory prosthesis 100 to boot or power up and to transmit a first status signal 522a to the apparatus 500. The first status signal 522a can be indicative of the status of the sound processor of the auditory prosthesis 100, which can include a programming status of the sound processor and a power status of the sound processor. In this example, the programming status of the sound processor can be the first programming status in which there are no operational parameter maps available (e.g., the auditory prosthesis 100 is booted or powered up for the first time) and the power status can be the first power status in which the sound processor is configured to receive power from an internal power source (e.g., the auditory prosthesis 100 comprises a totally implantable cochlear implant). The apparatus 500 can be configured to respond to the first status signal 522a by communicating the status of the sound processor to the clinician (e.g., the first programming status and the first power status).

In certain embodiments in which the programming status is stored locally in the data storage circuitry 230, the control circuitry 240 of the apparatus 200 retrieves the status from the data storage circuitry 230. In certain other embodiments in which the programming status is stored remotely (e.g., in the cloud), the control circuitry 240 retrieves the identification 250a from the data storage circuitry 230 and retrieves the status information 250b from the remote storage via the communication circuitry 260. The implanted portion of the auditory prosthesis 100 of certain embodiments accesses the remote status information 250b via the sound processor of the auditory prosthesis 100, while in certain other embodiments, the implanted portion of the auditory prosthesis 100 has a direct communication link with an accessory with internet access, thereby avoiding use of the sound processor as an intermediary.

The clinician can then access the user input mechanism 540 again to instruct the apparatus 500 to communicate a second control signal 512b to the auditory prosthesis 100, the second control signal 512b configured to instruct the auditory prosthesis 100 to initiate autonomous programming (e.g., NRT measurements to estimate at least one of a C-level profile and a T-level profile of the recipient) to generate an operational parameter map (e.g., a default operational parameter map). The auditory prosthesis 100 can further respond to the second control signal 512b by sending out one or more second status signals 522b to the apparatus 500, the one or more second status signals 522b indicative of the status of the sound processor with regard to the autonomous programming (e.g., whether the autonomous programming is currently being performed; whether the autonomous programming is currently encountering one or more problem conditions preventing proper operation of the autonomous programming; which of the operational parameter maps is being generated or modified by the autonomous programming; completion of the autonomous programming). The apparatus 500 can be configured to respond to the one or more second status signals 522b by communicating the corresponding statuses of the sound processor to the clinician. In certain embodiments, the clinician can command the apparatus 500 to enter a diagnostic mode or to command the auditory prosthesis 100 to enter a diagnostic mode in which the problem conditions are to be identified and/or solved.

In certain embodiments, the apparatus 500 can be used by a clinician and/or the recipient to initiate subsequent autonomous programming procedures (e.g., self-programming sessions) by the auditory prosthesis 100 (e.g., to select one of the operational parameter maps to be modified or improved by autonomous programming), to terminate and/or modify an autonomous programming procedure currently being run by the auditory prosthesis 100 (e.g., to manually override an aspect of an autonomous programming procedure that was automatically initiated), and/or to monitor a status of the auditory prosthesis 100 with regard to the autonomous programming (e.g., to detect error conditions or successful completions of autonomous programming procedures).

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. A method comprising:
   determining a programming status of a sound processor of an auditory device, the programming status indicative of whether one or more operational parameter maps are available to the sound processor; and
   selectively initiating autonomous programming of the sound processor based, at least in part, on the determined programming status of the sound processor, wherein the sound processor is configured to access the one or more operational parameter maps, and determining a programming status of the sound processor comprises determining whether the programming status of the sound processor is one of the following:
   a first programming status in which all of the one or more operational parameter maps are unavailable to the sound processor;
   a second programming status in which at least one but less than all of the operational parameter maps is unavailable to the sound processor; and
   a third programming status in which none of the operational parameter maps are unavailable to the sound processor.

2. The method of claim 1, wherein, when the programming status of the sound processor is the first programming status, the method further comprises using the autonomous programming to generate at least one of the unavailable operational parameter maps, and updating the programming status of the sound processor.

3. The method of claim 1, wherein, when the programming status of the sound processor is the second programming status, the method further comprises determining which of the operational parameter maps is unavailable to the sound processor.

4. The method of claim 3, wherein, when the programming status of the sound processor is the second programming status, the method further comprises using the autonomous programming to generate at least one of the unavailable operational parameter maps, and updating the programming status of the sound processor.

5. The method of claim 1, wherein, when the programming status of the sound processor is the third programming status, the method further comprises determining whether any of the operational parameter maps warrants improvement by autonomous programming.

6. The method of claim 5, wherein, when the programming status of the sound processor is the third programming status, the method further comprises using the autonomous programming to improve at least one of the operational parameter maps warranting improvement, and updating the programming status of the sound processor.

7. A method comprising:
   determining a programming status of a sound processor of an auditory device, the programming status indicative of whether one or more operational parameter maps are available to the sound processor;
   selectively initiating autonomous programming of the sound processor based, at least in part, on the determined programming status of the sound processor; and
   determining whether a power status of an implanted apparatus in communication with the sound processor is one of the following:
   a first power status in which the apparatus is configured to receive power from an internal power source configured to be continually operationally coupled to the apparatus; and
   a second power status in which the apparatus is configured to receive power from an external power source configured to be selectively operationally coupled to the apparatus.

8. The method of claim 7, wherein, when the power status of the apparatus is the first power status, selectively initiating autonomous programming is performed regardless of whether the apparatus is operatively coupled to the external power source.

9. The method of claim 7, wherein, when the power status of the apparatus is the second power status, selectively initiating autonomous programming is performed only when the apparatus is operatively coupled to the external power source.

10. An apparatus comprising:
    sound processing circuitry of an auditory device, the sound processing circuitry configured to access one or more signal processing data sets, to use at least one of the accessed signal processing data sets to process signals received from a microphone of the auditory device, and to generate stimulation signals transmitted to at least a portion of the auditory system of a recipient of the auditory device;
    data storage circuitry configured to store the one or more signal processing data sets; and
    control circuitry of the auditory device, the control circuitry configured to access information indicative of at least one of: a programming status of the auditory device indicative of whether one or more operational parameter maps are available to the control circuitry and a power status of the auditory device indicative of whether the control circuitry is configured to receive power from an internal power source or an external power source, the control circuitry further configured to selectively initiate, in response at least in part to the accessed information, autonomous programming of the auditory device to generate or modify at least one of the signal processing data sets.

11. The apparatus of claim 10, wherein the data storage circuitry further comprises the information and the control circuitry is configured to access the information from the data storage circuitry.

12. The apparatus of claim 10, wherein the information is indicative of the programming status of the auditory device, the programming status indicative of one or more statuses of the one or more signal processing data sets.

13. The apparatus of claim 12, wherein the data storage circuitry comprises one or more bytes configured to be read by the control circuitry to determine the programming status and further configured to be written to by the control circuitry to update the programming status stored by the data storage circuitry.

14. The apparatus of claim 10, wherein the information is further indicative of the identification of the auditory device, and the apparatus further comprises communication circuitry, the control circuitry further configured to access, via the communication circuitry, the programming status of the auditory device stored remotely from the apparatus and to update the programming status of the auditory device via the communication circuitry.

15. The apparatus of claim 10, wherein the one or more signal processing data sets comprise one or more of the following:
   a first signal processing data set configured to be used by the sound processing circuitry in normal sound environments;
   a second signal processing data set configured to be used by the sound processing circuitry in quiet sound environments;
   a third signal processing data set configured to be used by the sound processing circuitry in noisy sound environments;
   a fourth signal processing data set configured to be used by the sound processing circuitry in musical sound environments; and
   a fifth signal processing data set configured to be used by the sound processing circuitry during sleep of the recipient.

16. The apparatus of claim 10, further comprising at least one indicator configured to indicate to the recipient at least one of: whether the autonomous programming is currently being performed; whether the autonomous programming is currently encountering one or more problem conditions preventing proper operation of the autonomous programming; which of the one or more signal processing data sets is being generated or modified.

17. An apparatus comprising:
   at least one processor configured to generate at least one control signal;
   at least one communication link in operable communication with the at least one processor, the at least one communication link configured to transmit the at least one control signal to an implanted auditory device and to receive at least one status signal from the implanted auditory device, the implanted auditory device comprising a sound processor configured to transmit the at least one status signal indicative of a programming status of the sound processor, the programming status indicative of whether one or more operational parameter maps are available to the at least one processor, and to perform, in response to the at least one control signal, autonomous programming to generate or modify at least one operational parameter map;
   at least one indicator in operable communication with the at least one processor, the at least one indicator configured to communicate, in response to the received at least one status signal, the programming status of the sound processor to at least one of a recipient of the implanted auditory device and a clinician; and
   at least one user input mechanism in operable communication with the at least one processor, the at least one user input mechanism configured to be utilized by the at least one of the recipient and the clinician to provide at least one user input signal to the at least one processor, the at least one processor configured to respond to the at least one user input signal by generating the at least one control signal.

* * * * *